United States Patent [19]

Kotick et al.

[11] 4,259,329
[45] Mar. 31, 1981

[54] 17-CYCLOBUTYLMETHYL-3-HYDROXY-8β-METHYL-6-METHYLENE MORPHINANE, AND METHODS OF TREATING PAIN WITH THEM

[75] Inventors: Michael P. Kotick; Joseph O. Polazzi, both of Elkhart, Ind.

[73] Assignee: Miles Laboratories, Inc., Elkhart, Ind.

[21] Appl. No.: 138,102

[22] Filed: Apr. 21, 1980

Related U.S. Application Data

[63] Continuation-in-part of Ser. No. 85,774, Oct. 17, 1979, abandoned.

[51] Int. Cl.³ .................. A61K 31/485; C07D 221/28
[52] U.S. Cl. ........................................ 424/260; 546/75
[58] Field of Search ........................... 546/74; 424/260

[56]  References Cited

U.S. PATENT DOCUMENTS

| 3,285,922 | 11/1966 | Gates, Jr. | 546/74 |
| 3,654,280 | 4/1972 | Sawa et al. | 546/74 |
| 3,738,989 | 6/1973 | Sawa et al. | 546/74 |

FOREIGN PATENT DOCUMENTS

| 40-9268 | 5/1965 | Japan | 546/74 |
| 40-10153 | 5/1965 | Japan | 546/74 |
| 40-10216 | 5/1965 | Japan | 546/74 |

OTHER PUBLICATIONS

Sawa et al., Tetrahedron, vol. 24, pp. 255–260 (1968).

Primary Examiner—Donald G. Daus
Assistant Examiner—Diana G. Rivers
Attorney, Agent, or Firm—Jerome L. Jeffers

[57]  ABSTRACT

Disclosed are 6-methylene-morphinan compounds corresponding to the formula:

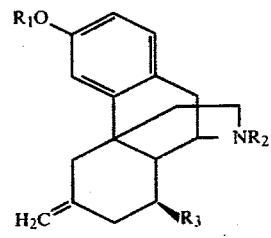

wherein $R_1$ and $R_3$ are H or methyl and $R_2$ is cyclopropylmethyl or cyclobutylmethyl. These compounds are useful as mixed analgesics/narcotic antagonists.

6 Claims, No Drawings

17-CYCLOBUTYLMETHYL-3-HYDROXY-β-METHYL-6-METHYLENE MORPHINANE, AND METHODS OF TREATING PAIN WITH THEM

BACKGROUND OF THE INVENTION

This application is a Continuation-in-Part of co-pending Application Ser. No. 85,774 filed Oct. 17, 1979, now abandoned.

FIELD OF THE INVENTION

Morphine is a well known narcotic analgesic having the structural formula:

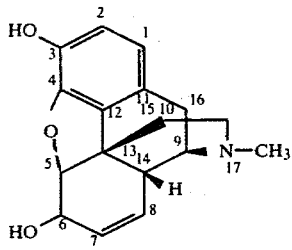

The compounds of this invention are structurally related to morphine and are named according to the morphinan system of nomenclature using the morphinan nucleus which is shown below:

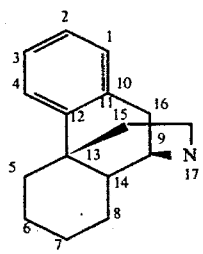

The numbering and stereochemical placement of atoms in the morphinan system is the same as that depicted for morphine. A dashed line is used to represent a covalent bond projecting below the plane of a reference atom while a wedged or heavily accented line signifies a covalent bond above such plane. The compounds of this invention have the same stereochemical placement of atoms as depicted for morphine in those positions where the stereochemistry is not depicted by a dashed or wedged line.

Morphine and its structurally related relatives are used primarily as analgesics. While extremely effective for the relief of moderate to severe pain these compounds are narcotic and most possess dependence-inducing ability and produce other side effects such as emesis, constipation, sweating, respiratory depression and myosis which make them less than ideal analgesics. It is impossible to predict, based on structure alone, whether a particular morphine-like compound will act as an analgesic (agonist), a narcotic antagonist or possess a combination of these properties since very minute structural modifications in the molecule result in significant changes in pharmacological activity. A compound with the appropriate profile of analgesic (agonist) and narcotic antagonist actions has potential for treatment of moderate to severe pain without the liability of drug dependence or drug abuse. Those compounds which are pure analgesics are useful in the treatment of acute pain.

PRIOR ART

The morphinan nucleus has been modified by the introduction of a carbonyl group into the 6-position and the conversion of the 3-hydroxy group to 3-methoxy. In this regard, Sawa et. al., report the preparation of 7,8-didehydro-3-methoxy-17-methylmorphinan-6-one in Tetrahedron 20:2247 (1964). Sawa et. al., also report narcotic antagonist activity for certain 17-allyl, 17-dimethylallyl or 17-cyclopropylmethyl substituted 3-hydroxy-morphinan-6-one compounds in U.S. Pat. No. 3,654,280 issued Apr. 4, 1972. West German laid open Application No. 29 00 644 discloses 8-alkyl substituted 3-hydroxy- or 3-methoxy-morphinan-6-one compounds which possess mixed analgesic/narcotic antagonist activity.

The preparation of the 6-methylene derivative of the narcotic antagonists naloxone and naltrexone has been reported by Hahn et al in *J. Med. Chem.*, 18, 259 (1975) to provide compounds of the formula:

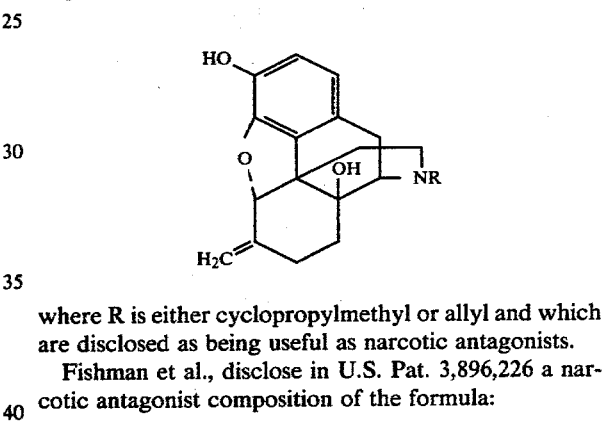

where R is either cyclopropylmethyl or allyl and which are disclosed as being useful as narcotic antagonists.

Fishman et al., disclose in U.S. Pat. 3,896,226 a narcotic antagonist composition of the formula:

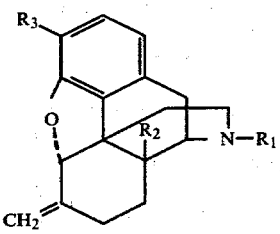

where $R_1$ is allyl or cyclopropylmethyl, $R_2$ is hydrogen or hydroxy and $R_3$ is hydroxy or methoxy.

J. Fishman discloses in U.S. Pat. No. 3,162,639 6-desoxy-14-hydroxy-dihydromorphine derivatives of the formula:

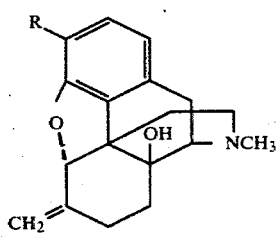

where R is —OCH$_3$ or OH. These compounds are described as being useful as narcotic, analgesic and sedative agents.

SUMMARY OF THE INVENTION

The present invention involves a series of 17-cycloalkylmethyl-3-hydroxy-or-methoxy-6-methylene-morphinanes characterized by the formula:

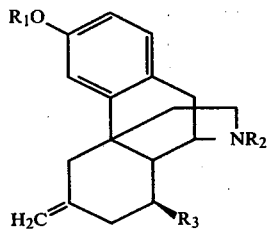

wherein R$_1$ and R$_3$ are H or methyl and R$_2$ is cyclopropylmethyl or cyclobutylmethyl.

DETAILED DESCRIPTION

The 6-methylene morphinan compounds of the present invention are prepared by reacting, in an inert solvent and under an inert atmosphere, methylenetriphenylphosphorane with a 6-keto morphinan of the formula:

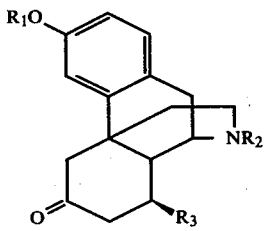

wherein R$_1$, R$_2$ and R$_3$ are as previously defined. The preparation of the 6-keto morphinan precursors is fully described in co-pending U.S. Application Ser. No. 40,664 filed May 21, 1979 whose specification is incorporated herein by reference. The compounds of this invention are useful as analgesics and as mixed analgesics/narcotic antagonists. In addition, a particular compound of this series (TR-5379) was found to have a steeper dose-response curve and a more potent morphine antagonist action than its corresponding 6-keto analog. Furthermore, this compound did not substitute for morphine in drug dependent rats or monkeys thereby indicating an unexpected pharmacological difference when compared to the 6-keto compound having similar substituents.

The preparation and pharmacology of the compounds of the present invention is further illustrated by the following examples:

EXAMPLE I 17-cyclopropylmethyl-3-methoxy-8β-methyl-6-methylene-morphinane (TR-5412)

A solution of methylenetriphenylphosphorane was prepared from sodium hydride (14.4 mmole) and methyltriphenylphosphonium bromide (5.14 g, 14.4 mmole) in dimethyl sulfoxide (30 ml) under an argon atmosphere. To this was added a solution of 17-cyclopropylmethyl-3-methoxy-8β-methylmorphinan-6-one (2.04 g, 6 mmole) dissolved in dimethyl sulfoxide (20 ml) and the reaction mixture stirred at 75° C. in an oil bath for 1 hour. The cooled solution was diluted with ice and concentrated NH$_4$OH and extracted with three portions of toluene. The combined toluene extracts were washed four times with water, dried and evaporated to a crude residue. The residue was chromatographed over Silica Gel G (400 g) using 20:1 chloroform-methanol as the eluent. Fractions were combined on the basis of thin layer chromatography to give 1.60 g (80%) of the desired product as a crystalline solid. Recrystallization form ether-hexane gave pure TR-5412, mp 91°–93°. NMR(CDCl$_3$): δ7.17–6.56, 3H, multiplet, aromatic; 4.67, 2H, broad singlet, methylene; 3.80, 3H, singlet, CH$_3$O—; 0.93, 3H, unsymmetrical doublet, 8β-CH$_3$; 0.8–07, cyclopropyl protons.

Anal. Calcd. for C$_{23}$H$_{31}$NO: C, 81.85; H, 9.26; N, 4.15. Found: C, 82.22; H, 9.29; N, 4.12.

EXAMPLE II

17-Cyclopropylmethyl-3-hydroxy-8β-methyl-6-methylene-morphinane (TR-5413)

A solution of methylenetriphenylphosphorane (14.4 mmole) in dimethyl sulfoxide (30 ml) was prepared under argon as described above. To this was added a solution of 17-cyclopropylmethyl-3-hydroxy-8β-methylmorphinan-6-one (1.95 g, 6 mmole) in dimethyl sulfoxide. Processing as described above gave a residue which was chromatographed to give 406 mg (20.4%) of the product as a crystalline solid. Recrystalliation from ethanol gave pure TR-5413, mp. 231°–233°.

Anal. Calcd. for C$_{22}$H$_{29}$NO: C, 81.69; H, 9.04; N, 4.33. Found: C, 81.81; H, 9.39; N, 4.16.

EXAMPLE III 17-cyclobutylmethyl-3-methoxy-8β-methyl-6-methylene-morphinane Hydrochloride (TR-5377)

To a solution of methylenetriphenylphosphorane (14.4 mmole) in dimethyl sulfoxide (30 ml) prepared in the usual fashion was added a solution of 17-cyclobutylmethyl-3-methoxy-8β-methyl-morphinan-6-one. The reaction was heated at 75° for 2 hours under an atmosphere of nitrogen. Workup followed by chromatography gave the free base of TR-5377 as a foam. This was converted to the HCl salt which was crystallized from toluene to give 860 mg (37%) of TR-5377, mp. 221°–224°.

Anal.: Calcd for C$_{24}$H$_{33}$NO.HCl: C, 74.30, H, 8.83; N, 3.61. Found: C, 74.62; H, 8.69; N, 3.56.

EXAMPLE IV

17-Cyclobutylmethyl-3-hydroxy-8β-methyl-6-methylene morphinane (TR-5379)

A solution of methylenetriphenylphosphorane was prepared from sodium hydride (14.4 mmole) and methyltriphenylphosphonium bromide (5.14 g, 14.4 mmole) in dimethyl sulfoxide (30 ml) under an argon atmosphere. To this was added a solution of 17-cyclobutylmethyl-3-hydroxy-8β-methylmorphinan-6-one (free base of TR-5257, 2.02 g, 6 mmole) in dimethyl sulfoxide (20 ml) and the reaction mixture stirred at 80° in an oil bath for one hour. The cooled solution was diluted with ice and concentrated NH$_4$OH and extracted with three portions of toluene. The combined toluene extracts were washed with four portions of water, dried and evaporated to crude residue. This residue was chromatographed over Silica Gel G (400 g) using 20:1 chloroform-methanol containing 0.5% concentrated NH₄OH as the eluant. Fractions were combined on the basis of thin layer chromatography to give 1.65 g (82%) of the desired product as a crystalline solid. Recrystallization from ether-hexane gave analytically pure product, mp 165°–169°.

Anal. Calcd. for $C_{23}H_{31}NO$: C, 81.85; H, 9.26; N, 4.15. Found: C, 82.01, H, 9.08; N, 3.92.

EXAMPLE V

17-Cyclobutylmethyl-3-hydroxy-8β-methylmorphinan-6-one Tartrate (TR-5257)

To a stirred solution of d-tartaric acid (16.09, 106 mmole) in ethanol (100 ml) was added dropwise a solution of 17-cyclobutylmethyl-3-hydroxy-8β-methylmorphinan-6-one (TR-5130-free base, 32.0 g, 94 mmole) in ethanol (100 ml). After several minutes of stirring, a white solid began to precipitate. The slurry was stirred at room temperature for several hours and then kept in the cold overnight. The solid was collected, washed with cold ethanol followed by ether and dried at atmospheric pressure and 115° C. for one hour to give 32.0 g (69%) of TR-5257 as a white powder, mp. 210°–213° dec.

Anal. Calcd. for $C_{22}H_{29}NO_2 \cdot C_4H_6O_6$: C, 63.79; H, 7.21; N, 2.86. Found: C, 63.91; H, 7.25, N, 2.77.

EXAMPLE VI

17-Cyclobutylmethyl-3-hydroxy-6-methylene-morphinane Hydrochloride Acetone Solvate (TR-5566)

Reaction of 17-cyclobutylmethyl-3-hydroxy-morphinan-6-one (3.0 g, 9.2 mmole) with methylenetriphenylphosphorane (4 equivalents, 36.8 mmole) followed by chromatography of the residue gave 2.6 g (87%) of the free base of TR-5566 as a foam. The hydrochloride salt of TR-5566 was first crystallized from ethyl acetate and then acetone to give pure TR-5566, mp 155° (foams). The presence of acetone was confirmed by nuclear magnetic resonance spectroscopy of TR-5566 in dimethyl sulfoxide-d₆.

Anal. Calcd. for $C_{22}H_{29}NO \cdot HCl \cdot C_3H_6O$: C, 71.83; H, 8.68; N, 3.35. Found: C, 71.96; H, 8.55; N, 3.30.

EXAMPLE VII

17-Cyclopropylmethyl-3-hydroxy-6-methylene-morphinan (TR-5609)

Reaction of 17-cyclopropylmethyl-3-hydroxy-morphinan-6-one (1.58 g, 5 mmole) with methylenetriphenylphosphorane (20 mmole) in dimethyl sulfoxide gave a crude residue which was chromatographed using 10:1 chloroform-methanol containing 1% concentrated ammonium hydroxide. Pure fractions were pooled to give 909 mg (58%) of TR-5609 which crystallized from ethanol to give 532 mg of analytically pure TR-5609, mp 220°–223°.

Anal. Calcd. for $C_{21}H_{27}NO$: C, 81.51; H, 8.79, N, 4.53. Found: C, 81.44; H, 8.80; N, 4.30.

EXAMPLE VIII

17-Cyclobutylmethyl-3-methoxy-6-methylene-morphinane Tartrate Ethanol Solvate (TR-5610)

Reaction of 17-cyclobutylmethyl-3-methoxy-morphinan-6-one (3.39 g, 10 mmole) with methylenetriphenylphosphorane (40 mmole) in dimethyl sulfoxide gave a residue which was chromatographed using 30:1 chloroform-methanol containing 0.5% concentrated ammonium hydroxide. Fractions which contained only the desired product were pooled to give 866 mg (26%) of the free base of TR-5610 as a foam. This was converted to the d-tartrate salt which was crystallized from ethanol to give pure TR-5610, mp 88°–91°.

Anal. Calcd. for $C_{23}H_{31}NO \cdot C_4H_6O_6 \cdot C_2H_5OH$: C, 65.27; H, 8.12; N, 2.62. Found: C, 65.73; H, 7.92; N, 2.51.

PHARMACOLOGICAL EVALUATION

The compounds whose preparation are disclosed in the foregoing examples were screened to determine the following biological activities:

(A) Analgesic effects upon mice (acetic acid writhing test).

(B) Narcotic antagonist activity in rats (modified rat tail flick test).

TEST A

Acetic Acid Mouse Writhing Test

The analgesic effects of the test compounds were determined in mice by use of the acetic acid writhing test described by B. A. Whittle, Brit. J. Pharmacol., 22: 246 (1964). In this test at least three groups of 5 male CD-1 mice each were given subcutaneous doses of the test drug dissolved in distilled water. In all cases 0.4 milliliters of a 0.5% V/V acetic acid in distilled water solution was administered intraperitoneally 15 minutes post drug. The number of writhes in a 20 minute interval beginning 5 minutes after the acetic acid injection were determined and compared with the number of writhes in a control group which had received only acetic acid.

Percent inhibition of writhing was calculated as:

$$\% \text{ inhibition} = \left[ \frac{\text{No. Control Writhes} - \text{No. Treated Writhes}}{\text{No. Control Writhes}} \right]$$

The ED₅₀ dose, i.e., the dose required to reduce the number of writhes by 50%, was determined graphically from a plot of % inhibition as a probit verus log dose. Confidence limits of 95% were calculated on the basis of those results falling in the range 16–84% inhibition. See Litchfield, J. T. and Wilcoxon, F., J. Pharmacol. Exp. Ther., 96, 99–113 (1949).

TEST B

Evaluation of Narcotic Antagonist Activity

The narcotic antagonist effect of the test compound was determined by a modification of the rat tail flick procedure of Harris and Pierson (J. Pharmacol. Exp. Ther., 143:141 [1964]).

Male albino Wistar rats (100–120 g) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from two to four seconds. Animals with a control reaction time outside this range are rejected. The rheostat adjustment is made only if a significant proportion (1 out of every 10 rats) of the reaction times are outside the range of two to four seconds. Groups of 5 rats were used, and two control times were determined at 60 and 30 minutes prior to subcutaneous injection of the drug. A ten second cutoff time is employed; if the rat does not flick its tail in 10 seconds it is removed from the heat source.

At least thirty minutes after the last control run the test drug was given intraperitoneally. This was followed ten minutes later by an $ED_{80}$ dose of morphine subcutaneously. The animals were retested at 20 minutes after the morphine injection. Control animals were given vehicle and morphine only. The data were calculated as follows:

$$\% \text{ Effect } (E) = \left[ \frac{MRT^* \text{ (Treated)} - MRT \text{ (Control)} \times 100}{10 - MRT \text{ (Control)}} \right]$$

% Antagonism =

$$\left[ \frac{E \text{ (morphine control)} - E \text{ (Drug treated)} \times 100}{E \text{ (morphine control)}} \right]$$

*MRT is defined as mean reaction time.

The data were plotted on log-probit paper and $AD_{50}$ values, i.e., the dose required to inhibit the effect of morphine by 50% within 95% confidence limits, were determined by the method of Litchfield and Wilcoxon.

The results obtained using the foregoing procedures are set out in Table I where IA means inactive at the dose indicated.

TABLE I

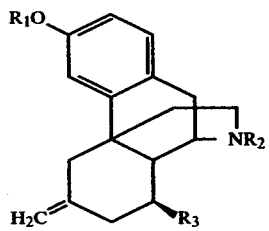

| Compound | Ex | $R_1$ | $R_2$ | $R_3$ | $ED_{50}$ (mg/kg) | $AD_{50}$ (mg/kg) |
|---|---|---|---|---|---|---|
| TR-5412 | I | $CH_3$ | CPM | $CH_3$ | 3.20 | 3.80 |
| TR-5413 | II | H | CPM | $CH_3$ | 1.70 | 0.29 |
| TR-5377 | III | $CH_3$ | CBM | $CH_3$ | 6.42 | 5.50 |
| TR-5379 | IV | H | CBM | $CH_3$ | 0.18 | 0.83 |
| *TR-5257 | V | H | CBM | $CH_3$ | 0.14 | 1.22 |
| TR-5566 | VI | H | CBM | H | 0.09 | >10 |
| TR-5609 | VII | H | CPM | H | 0.38 | 0.115 |
| TR-5610 | VIII | $CH_3$ | CBM | H | 1.60 | IA @ 10 |

CPM = cyclopropylmethyl
CBM = cyclobutyl methyl
*6-keto compound

TEST C

Substitution Studies in Physically Morphine Dependent Rats

Rats were made physically dependent by continuous infusion of morphine through an indwelling intraperitoneal cannula as has been described (D. G. Teiger, *J. Pharmacol. Exp. Ther.*, 190 408, 1974). Then one day substitution of either TR-5257 or TR-5379 was studied. Both drugs were infused at the rate of 125 mg/kg/day. Table II shows the change in body weights for both groups during this period of drug substitution for morphine. TR-5257 appeared to prevent the marked loss in weight observed in the morphine controls. There were, however, marked withdrawal symptoms during this period (Table III). The results obtained with TR-5379 are similar except that the initial loss in weight was closer to that seen with morphine. TR-5379 clearly does not substitute for morphine in rats at the doses used. The results with TR-5257 are ambiguous, with indication of partial substitution in this instance.

TABLE II

| | | | Mean % Change in Weight From Termination of Morphine Infusion | | | | | |
|---|---|---|---|---|---|---|---|---|
| DRUG | DOSE | N | +6 hr | +1 day* | +30 hr | +2 days | +3 days | +4 days |
| TR-5257 | 125 mg/kg/day for 1 day | 8 | −6.1 ±2.9 | −7.5 ±2.1 | −2.64 ±1.52 | −1.4 ±2.4 | −0. ±3.1 | +2.7 ±3.9 |
| TR5379 | 125 mg/kg/day for 1 day | 6 | −15.1 ±0.9 | −15.8 ±2.1 | −11.3 ±2.02 | −4.5 ±2.2 | −0.2 ±2.4 | — |
| Morphine | See Schedule Below | 8 | — | −16.8 ±1.3 | — | −12.7 ±1.9 | −7.8 ±2.3 | −1.6 ±1.6 |

*Test drug infusion stopped here.
Animals were infused with morphine according to the following schedule
50 mg/kg/day for 1 day
100 mg/kg/day for 1 day
200 mg/kg/day for 4 days

TABLE III

| INCIDENCE OF SIDE EFFECTS | |
|---|---|
| | TR-5257 |
| +6 hr* | 8/8 - Pilo erection |
| | 6/8 - Wet dog shakes |
| | 4/8 - Diarrhea |
| | 1/8 - Aggressive |
| +24 hr | 4/8 - Pilo erection |
| | 1/4 - Tremors |
| +30 hr | 4/8 - Pilo erection |
| | TR-5379 |
| +6 hr* | 6/6 - Pilo erection |
| | 4/6 - Diarrhea |
| | 1/6 - Aggresive |
| +24 hr | 6/6 - Pilo erection |
| | 2.6 - Diarrhea |
| +30 hr | 4/6 - Pilo erection |
| | 2/6 - Diarrhea |

*Post termination of morphine infusion and during test drug infusion.

Morphinan type compounds which possess both agonist and narcotic antagonist activity are of special interest because they can be used to treat pain without the liability of drug dependence in an individual to whom they are administered. The term "individual" is used herein to mean a human being or an experimental animal that is a model for a human being. The dose to be administered to achieve the desired result, i.e., the effective dose, may vary from individual to individual but is readily determined by one skilled in the art without undue experimentation.

The compounds of the present invention form pharmacologically active addition salts with organic and inorganic acids. Typical acid addition salts are the tartrate, hydrobromide, hydrochloride and maleate. The hydrochloride is preferred. The compounds of the present invention may be administered by known, conventional methods of therapeutic administration such as intravenous, parenteral, buccal, rectal or oral. Dose forms for the administration of these compounds can be prepared by methods recognized in the pharmaceutical sciences.

What is claimed is:

1. 17-cyclobutylmethyl-3-hydroxy-8β-methyl-6-methylene morphinane of the formula:

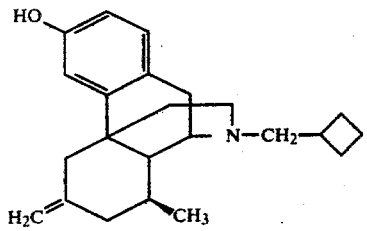

2. The compound of claim 1 in the form of its nontoxic, pharmaceutically acceptable acid addition salt.

3. The compound of claim 1 which is in the form of the tartrate, hydrobromide, hydrochloride or maleate salt.

4. A therapeutic method of treating pain in an individual requiring such treatment which comprises administering to such individual an effective amount of a compound characterized by the formula:

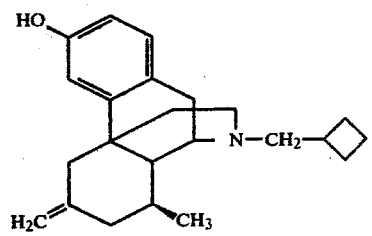

5. The method of claim 4 in which the compound is administered in the form of its nontoxic, pharmaceutically acceptable acid addition salt.

6. The method of claim 4 wherein the compound is in the form of its tartrate, hydrobromide, hydrochloride or maleate salt.

* * * * *